United States Patent [19]

Driscoll

[11] Patent Number: 5,087,284
[45] Date of Patent: Feb. 11, 1992

[54] 5-SUBSTITUTED THIADIAZOLE UREAS AND THEIR USE AS HERBICIDES

[75] Inventor: Patrick R. Driscoll, Spotswood, N.J.

[73] Assignee: Rhone-Poulenc, Inc., Monmouth Jct., N.J.

[21] Appl. No.: 428,489

[22] Filed: Oct. 31, 1989

Related U.S. Application Data

[60] Continuation of Ser. No. 487,750, Apr. 22, 1983, abandoned, which is a continuation of Ser. No. 299,858, Sep. 19, 1981, abandoned, which is a continuation of Ser. No. 79,413, Sep. 27, 1979, abandoned, which is a continuation of Ser. No. 316,794, Dec. 20, 1972, abandoned, which is a division of Ser. No. 296,389, Oct. 10, 1972, abandoned, which is a continuation-in-part of Ser. No. 71,248, Sep. 10, 1970, abandoned, which is a division of Ser. No. 818,078, Apr. 21, 1969, abandoned, which is a continuation-in-part of Ser. No. 782,756, Dec. 10, 1968, abandoned, which is a continuation-in-part of Ser. No. 702,189, Feb. 1, 1968, abandoned.

[51] Int. Cl.$^5$ .................................. A01N 43/82
[52] U.S. Cl. ........................... 71/90; 546/209; 548/140
[58] Field of Search ..................... 71/90; 548/140

[56] References Cited

U.S. PATENT DOCUMENTS

| 4,049,670 | 9/1977 | Metzger et al. | 548/140 |
| 4,876,044 | 10/1989 | Cebalo et al. | 71/90 |

FOREIGN PATENT DOCUMENTS

| 0743614 | 6/1970 | Belgium | 71/90 |
| 743615 | 6/1970 | Belgium | 548/140 |

Primary Examiner—Glennon H. Hollrah
Assistant Examiner—Susan P. Treanor
Attorney, Agent, or Firm—Scully, Scott, Murphy & Presser

[57] ABSTRACT

New thiadiazole ureas are provided for the control of plant growth, especially of undesirable weeds and grasses. Particularly effective are compounds which contain an organic substituent in the 5-position of the thiadiazole portion.

9 Claims, No Drawings

5-SUBSTITUTED THIADIAZOLE UREAS AND THEIR USE AS HERBICIDES

CROSS-REFERENCE TO RELATED APPLICATIONS

This application is a continuation, of application Ser. No. 487,750, filed Apr. 22, 1983, now abandoned, which is a continuation of application Ser. No. 299,858, filed Sept. 8, 1981, now abandoned, which is a continuation of application Ser. No. 079,413 filed Sept. 27, 1979, now abandoned, which is a continuation of Ser. No. 316,794 filed Dec. 20, 1972, now abandoned, which is a division of Ser. No. 296,389 filed Oct. 10, 1972, now abandoned, which is a continuation-in-part of Ser. No. 071,248 filed Sept. 10, 1970, abandoned, which is a division of Ser. No. 818,078 filed Apr. 21, 1969, abandoned, which is a continuation-in-part of Ser. No. 782,756 filed Dec. 10, 1968, abandoned, which is a continuation-in-part of Ser. No. 702,189 filed Feb. 1, 1968, abandoned.

BACKGROUND OF THE INVENTION

1. Field of the Invention

This invention relates to new compositions of matter and to a method of controlling plant growth therewith. More particularly, it relates to new thiadiazole ureas and to the control of plant growth, especially of undesirable plants, with the new compounds.

2. Description of the Prior Art

As is well known to those familiar with this art effective control of undesired vegetation governs, to a large degree, yields from food crops. When weeds and other unwanted plants are controlled, one source of competition for the available moisture, nutrients, sunlight and the like is eliminated. Furthermore, effective control also increases the efficiency of maintenance along roadways and railroad tracks, near industrial buildings, along power rights-of-way and the like.

The problems associated with effective control of undesired plants in each of the named areas are quite different. For example, when treating crops, or land which is being prepared for crops, the herbicide chosen should be selective in its activity. That is, it should be able to kill weeds and other unwanted plants, but it must be harmless to the food crop plant growing or to be grown in the treated area. When treating certain other areas such as under power lines, it may be helpful to kill all plant life, and a herbicide which is non-selective will be most useful in this application.

Chemical herbicides are classified generally according to the type of activity possessed thereby. A given compound may possess more than one type of activity depending upon its mode of application and the rate at which it is applied. In addition, herbicides are usually classified as selective or non-selective pre-emergents or post-emergents. The former are applied to the soil before the seeds germinate, and to be effective they must be in intimate contact with the seeds, or with the germinated seedlings. Since weed seeds will germinate closer to the ground than crop seeds, a non-selective pre-emergence herbicide can be effectively used if its penetration is limited to a depth above the crops seeds. Since this is not always possible, the most effective pre-emergence herbicide is one which is selective in its nature. If the selected compound will kill the seed and germinated seedlings of undesirable plants without harm to the seed and germinated seedlings of the crop, there will not be any danger from overpenetration.

Post-emergence herbidides, on the other hand, are applied after the crop and weeds have attained substantial height. Generally speaking, if a compound is found to have post-emergence activity it will not be selective. This is in keeping with the observation that, as a rule, herbicidally active compounds will not be selective in their action on plant life.

The prior art, for example, in an article by S. Giri and H. Singh, J. Indian Chem. Soc., 43 (7), 477-80 (1966), discloses certain 1,3-di-substituted ureas, sulfonyl-ureas and related compounds. Another reference, an article by A. Ermili and I. Cortese, Formaco (Pavio), Ed. Sci., 18 (8), 607-13 (1963), see C. A. 60, 2208c (1964), discloses such compounds as 1-(1, 3, 4-thiadiazol-2-yl)-3-(p-toluenesulfonyl) urea and 1-(5-methyl-1,3,4-thiadiazol-2-yl)-3-(p-toluenesulfonyl) urea. This art does not disclose herbicidal activity for the compounds taught therein. No art is known which does teach herbicidal activity for the referenced compounds or for the compounds to be more fully described in this application.

The starting materials for many of the compounds embraced in the present invention are 2-amino or alkylamino-5-substituted-1, 3, 4-thiadiazoles. These starting materials may be prepared in accordance with the method of Lazari and Sharghi, J. of Het. Chem., 3, 336 (1966), or by other known literature methods.

SUMMARY OF THE INVENTION

In accordance with the invention, there is provided a compound of the formula:

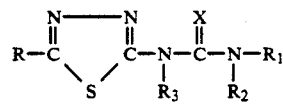

wherein R is selected from the group consisting of H, alkyl ($C_1$-$C_6$), haloalkyl ($C_1$-$C_6$), cycloalkyl ($C_3$-$C_6$), halocycloalkyl ($C_3$-$C_6$), alkoxy, alkoxyalkyl, alkoxyalkylthio, aryl, substituted aryl (e.g., haloaryl, haloalkylaryl, alkylaryl), alkenyl ($C_2$-$C_6$), alkylthio ($C_1$-$C_{12}$), alkenylthio ($C_2$-$C_{12}$), alkynylthio ($C_2$-$C_{12}$), benzylthio, substituted benzylthio, phenylalkylthio, epoxyalkylthio, haloalkyl ($C_1$-$C_{12}$)thio, haloalkenyl ($C_{2-12}$)thio, cyanoalkylthio, oxocyclohexylthio, carbalkoxyalkylthio, alkoxyacylalkylthio, thiocyanoethylthio, cycloalkyl ($C_3$-$C_{12}$)thio, phenylalkenylthio, arylthio, substituted arylthio, acylalkylthio, heteroarylthio, aminoalkylthio, dialkyl($C_1$-$C_{12}$)aminoalkylthio, aziridinylalkylthio, alkylsulfoxide ($C_1$-$C_6$), and alkylsulfonyl ($C_1$-$C_6$); $R_1$ is selected from the group consisting of H, alkyl ($C_1$-$C_4$), and cycloalkyl ($C_3$-$C_6$); $R_2$ is from the group consisting of H, alkyl ($C_1$-$C_4$), haloalkyl ($C_1$-$C_4$), alkoxy ($C_1$-$C_4$), alkenyl ($C_2$-$C_4$), alkynyl ($C_2$-$C_4$), aryl and haloaryl, and wherein $R_1$ and $R_2$ are alkylene which, together with N, form a ring of at least 3, but not more than 6 members; $R_3$ is H or alkyl ($C_{1-6}$); and X is selected from the group consisting of oxygen and sulfur.

In accordance with the invention also, a method is provided for controlling plant growth which comprises applying to said plant or to the seed thereof a growth controlling amount of a thiadiazole urea as above defined.

DESCRIPTION OF SPECIFIC EMBODIMENTS

The thiadiazole ureas of the present invention are stable and well-defined, and are particularly suited for herbicidal use when employed alone or in combination with inert carriers generally utilized in the herbicide art. The carrier adjuvants may be liquid or solid, depending upon the area to be treated, the type of plant to be controlled, and the kind of equipment available for application. When employing liquid formulations, they may be in the form of true solutions, dispersions, or emulsions containing, preferably, a small amount of a wetting agent. The compositions will contain a minor, herbicidal amount of compound and a major amount of the carrier thereof.

It is noted that the compounds useful in the invention are generally water insoluble, thus requiring an organic solvent when true solutions are desirable or necessary. Acetone, for example, can be used as the solvent. Others will be obvious to those skilled in the art, and need not be set forth herein.

When dispersions are used, the dispersive medium will generally be essentially aqueous, but it may contain small quantities of organic solvent, i.e., amounts not sufficient to cause solution of the active member, as well as a small amount of a wetting agent to aid in holding the particles in suspension.

The wetting agents referred to, in addition to aiding in suspending the toxic particles, are useful as aids in uniformly distributing the active material over the area to be treated. In other words, the wetting agents helps to prevent build-up of droplets on certain portions of the area, whereupon other portions are left untouched or insufficiently treated by the toxicant. These agents are well known to the art and it would serve no useful purpose to enumerate them here. One example, however, of a useful wetting agent is Tween-20, a polyethylene sorbitan monolaurate.

Solid formulations contemplated can be dusts or granules containing herbicidal amounts of the disclosed thiadiazole ureas. Many solids are known by the art to be useful as herbicidal carriers. Examples of these are kaolin, talc, kieselguhr, diatomaceous earth, pyrophyllite, bentonite, calcium carbonate, powdered cork, wood, walnut shells and peanut shells, Fuller's earth, tricalcium phosphate, and the like. Formulations using these carriers can be prepared in known ways.

Additionally, the inventive compounds can be applied as aerosols, in which case it is convenient to dissolve them in any suitable solvent and to disperse this solution in dichlorofluoromethane or other chlorofluoroalkane having a boiling point below room temperature at ambient pressure. It is contemplated that other suitable materials boiling below room temperature will also be useful for this purpose.

The concentration of the chemicals in the compositions disclosed herein can vary over a wide range provided a herbicidal or toxic dosage thereof is placed upon the plant or in its immediate surroundings. Thus, the important consideration is not minimum and maximum concentrations, but the most economical concentration. The inventive herbicides are effective over the range of from about 0.25 pound to about 30 pounds of active ingredient per acre treated, and the most suitable ratio of carrier to active ingredient will be governed by the amount of carrier needed to give an even distribution of a growth controlling quantity of active material over the area under treatment.

In controlling undesirable plants with the disclosed chemicals as pre-emergents, the toxicant or compositions containing it can be sprayed (if a liquid) or spread (if a solid) over the ground. Thereafter, the material can be left to the neutral action of rainfall, or it can be drenched or plowed and disked into the soil. When used as postemergents, a solid formulation can be dusted into the plants by the same method used to apply other well known solid herbicidal compositions. When liquid sprays are employed to treat plants, the liquid composition can be sprayed thereon just to the point of liquid run-off.

Having described the invention in general terms, the following Examples of the chemicals of this invention and their use as herbicides are offered. It will be understood that the Examples given merely illustrate the invention by way of specific embodiments, and thus are not to be construed as limitations upon it. To the contrary, the invention is to be limited only to the extent of the broader definition set forth hereinbefore and the appended claims. In the Examples "parts" are parts by weight unless otherwise designated.

EXAMPLE 1

1-Methyl-3-[5-Trifluoromethyl-2-(1, 3, 4-Thiadiazolyl)] Urea

Five parts, 0.03 mole, of 2-amino-5-trifluoromethyl-1, 3, 4-thiadiazole was dissolved in 45 parts of pyridine in a pressure bottle. 4.9 Parts, 0.033 mole, of methyl isocyanate was added and the mixture was heated in a steam bath for 2½ hours. After this heating period, the pyridine was removed by distillation under reduced pressure to a final pressure of 20 mm. and a final temperature of 75° C. A yellow solid residue was obtained and was recrystallized from ethanol-water to give a white solid weighing 4.2 parts (61.9% yield). The product had a melting point of 192°–193° C., and its IR and NMR spectra supported the proposed structure.

| Analysis: | Found | Calculated |
|---|---|---|
| Carbon (C), % | 26.31 | 26.55 |
| Hydrogen (H), % | 2.08 | 2.23 |
| Nitrogen (N), % | 24.52 | 24.77 |

EXAMPLE 2

1, 1-Dimethyl-3-[5-Trifluoromethyl-2-(1, 3, 4-Thiadiazolyl)] Urea 4.4 Parts, 0.074 mole, of carbonyl sulfide was bubbled into 87 parts of toluene. 6.7 Parts, 0.15 mole, dimethylamine was added at a temperature of 10°–15° C. over a period of 30 minutes. 6.3 Parts, 0.037 mole, of 2-amine 5-trifluoromethyl-1, 3, 4-thiadiazole was added to this mixture and the mixture was refluxed for 16 hours. After refluxing to complete the reaction, the resulting mixture was cooled and the toluene was removed by distillation under reduced pressure to a final temperature of 75° and a final pressure of 20 mm. An orange solid residue was obtained and this was recrystallized from benzene to give 3.3 parts (37.7% yield) of a tan solid. The product thus obtained had a melting point of 157°–58° C. and the IR and NMR spectra supported the proposed structure.

Analysis: N,% 23.02, found 23.32, calculated.

EXAMPLE 3

1-Methyl-3-[5-Ethyl-2-(1, 3, 4-Thiadiazolyl)] Urea

Using essentially the same procedure as described in Example 1, 10.0 parts, 0.078 mole, of 2-amino-5-ethyl-1,3,4-thiadiazole gave 7.4 parts (51% yield) of the product in the form of a white solid melting at 188°–89° C. The IR and NMR Spectra supported the proposed structure.

Analysis: N,% 30.10, found 30.10, calculate

EXAMPLE 4

1,1,3-Trimethyl-3-[5-Trifluoromethyl-2-(1,3,4-Thiadiazolyl)] Urea

2-Methylamino-5-trifluoromethyl-1,3,4-thiadiazole (6.0 g, 0.033 mole, m.p. 116°–18° C.), prepared by reaction of 4-methylthiosemicarbazide with trifluoroacetic acid in polyphosphoric acid, was dissolved in pyridine (50 ml). Dimethylcarbamyl chloride (3.5 g, 0.033 mole) was added dropwise to the resulting mixture and a light yellow solution resulted. The mixture so formed was heated at 89° C. for 90 hours, cooled and poured into 100 ml of water. The water solution was extracted with $2 \times 100$ ml of $CH_2Cl_2$ and the $CH_2Cl_2$ was washed with $4 \times 100$ ml of 5% aqueous HCl followed by $4 \times 100$ ml of water. The $CH_2Cl_2$ solution was dried over anhydrous $CaSO_4$ and removed by distillation under reduced pressure. A white crystalline solid residue was obtained. The residue was slurried with hexane and filtered. After drying in a vacuum desiccator the residue weighed 3.3 g (40% yield), m.p. 59°–61°.

Analytical results for the residue are:

|   | Calculated | Found |
|---|---|---|
| C | 33.07% | 33.08% |
| H | 3.57% | 3.69% |

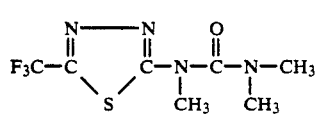

EXAMPLE 5

The compound 1,1,3-trimethyl-3-[5-methylthio-3-(1,3,4-thiadiazolyl)] urea can be prepared in a manner similar to that described in EXAMPLE 4 by using 2-methylamino 5-methylthio-1,3,4-thiadiazole (melting point, 85°–87° C.). The compound is recovered in the form of a brown oil.

The following compounds shown in TABLE I are prepared in accordance with the methods shown in EXAMPLES 1 to 3, and are suitable for use as herbicides.

TABLE I $$\begin{array}{c} N\!\!=\!\!\!=\!\!N \quad\; X \\ \| \quad\quad \| \quad\; \| \\ R\!-\!C \quad\; C\!-\!N\!-\!C\!-\!N\!-\!R_1 \\ \;\backslash\, /\quad\quad |\quad\; | \\ \;\; S \quad\; H \quad R_2 \end{array}$$

| EXAMPLE | R | $R_1$ | $R_2$ | X | M. Pt., °C. |
|---|---|---|---|---|---|
| 9 | $CF_3$ | $C_2H_5$ | H | O | 185–6 |
| 10 | $CF_3$ | $C_3H_7$ | H | O | 163–5 |
| 11 | $CF_3$ | $(H_3C)_2CH$ | H | O | 164–5 |

TABLE I-continued $$\begin{array}{c} N\!\!=\!\!\!=\!\!N \quad\; X \\ \| \quad\quad \| \quad\; \| \\ R\!-\!C \quad\; C\!-\!N\!-\!C\!-\!N\!-\!R_1 \\ \;\backslash\, /\quad\quad |\quad\; | \\ \;\; S \quad\; H \quad R_2 \end{array}$$

| EXAMPLE | R | $R_1$ | $R_2$ | X | M. Pt., °C. |
|---|---|---|---|---|---|
| 12 | $CF_3$ | $H_2C=CHCH_2$ | H | O | 154–8 |
| 14 | $CF_3$ | $C_6H_5$ | H | O | 252–3 |
| 15 | $CF_3$ | Cl—⌬— | H | O | 270–1 |
| 16 | $CF_3$ | Cl—⌬— (with Cl) | H | O | 241–2 |
| 18 | $CH_3$ | $CH_3$ | H | O | 267 (decomp.) |
| 19 | $CH_3$ | $CH_3$ | $CH_3$ | O | 192–4 |
| 20 | $C_2H_5$ | $CH_3$ | $CH_3$ | O | 151–2 |
| 21 | $(H_3C)_2CHCH_2$ | $CH_3$ | H | O | 156–7 |
| 24 | $H_3CO$ | $CH_3$ | H | O | 185–7 |
| 25 | $H_3COCH_2$ | $CH_3$ | H | O | 175–7 |
| 26 | $H_3CS$ | $CH_3$ | H | O | 210 |
| 28 | $H_3CS$ | $C_2H_5$ | H | O | 191–2 |
| 29 | $H_3CS$ | $C_3H_7$ | H | O | 140–1 |
| 30 | $H_3CS$ | $(H_3C)_2CH$ | H | O | 175–8 |
| 31 | $H_3CS$ | $H_2C=CHCH_2$ | H | O | 150–2 |
| 32 | $H_5C_2S$ | $CH_3$ | H | O | 198–9 |
| 33 | $H_3CSO_2$ | $CH_3$ | H | O | 224 (decomp.) |
| 34 | $C_6H_5$ | $CH_3$ | H | O | 210 |
| 35 | H | $CH_3$ | H | O | 224 (decomp.) |

Additional compounds illustrating the invention are those represented by the general formula given Table I and indicated directly below. They can be prepared by methods corresponding to those shown in EXAMPLES 1–3.

| R | $R_1$ | $R_2$ | X |
|---|---|---|---|
| $CF_3$ | $CH_3$ | H | S |
| $CF_3$ | $CH_3$ | $CH_3$ | S |
| $CF_3$ | $CH_3$ | $OCH_3$ | O |
| $CF_3$ | n-$C_4H_9$ | $C_2H_5$ | O |
| $CF_3$ | $+CH_2CH_2+$[1] |  | O |
| $H_2C=CH$ | $CH_3$ | H | O |
| $\begin{array}{c}H_2C\!\!\searrow\\ \quad\; \big|\;CH\\ H_2C\!\!\nearrow\end{array}$ | $CH_3$ | H | O |
| $H_3CS$ | $CH_3$ | $CH_3$ | O |

[1] $R_1$ and $R_2$ are part of a cyclic structure with N.

Additional compounds are the following in which $R_1$ is H, $R_2$ is $CH_3$, X is O, and R is one of the following groups:

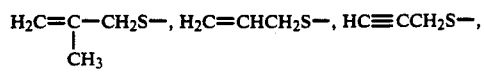

-continued

C₆H₅CH₂S—, 2,4-dichlorobenzylthio, H₂C—CH—CH₂S—,
\\ /
O

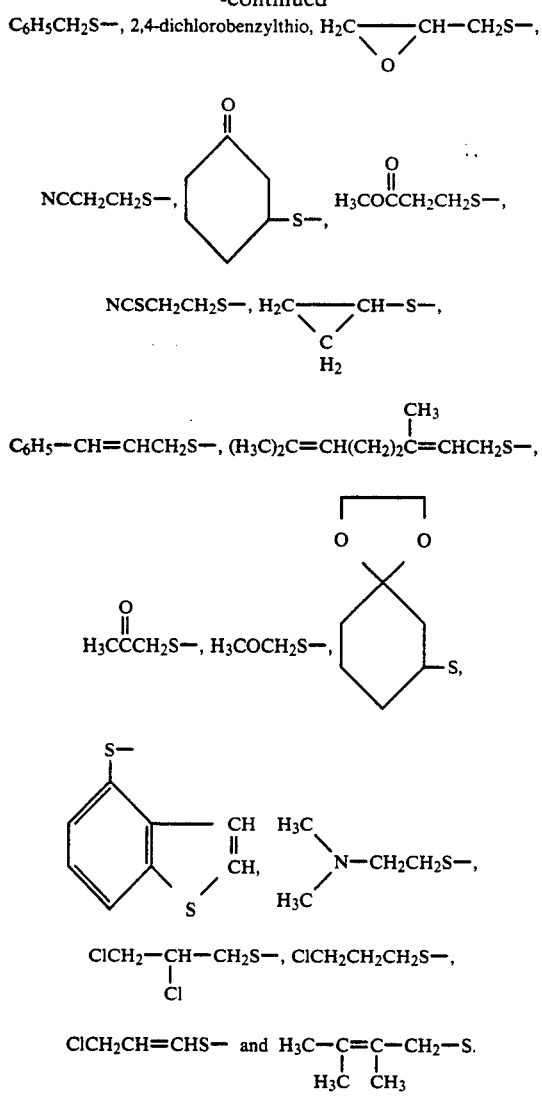

NCCH₂CH₂S—,

H₃COCCH₂CH₂S—, (with C=O)

NCSCH₂CH₂S—, H₂C—CH—S—,
\\ /
C
H₂

C₆H₅—CH=CHCH₂S—, (H₃C)₂C=CH(CH₂)₂C(CH₃)=CHCH₂S—,

H₃CCCH₂S— (with C=O), H₃COCH₂S—,

ClCH₂—CH—CH₂S—, ClCH₂CH₂CH₂S—,
|
Cl

ClCH₂CH=CHS— and H₃C—C=C—CH₂—S.
| |
H₃C CH₃

The following compounds shown in TABLE II are prepared in keeping with the method of EXAMPLE 1, and are also suitable for use as herbicides.

TABLE II

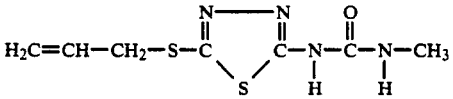

| EXAMPLE | R | $R_1$ | $R_2$ | $R_3$ | M. Pt., °C. |
|---|---|---|---|---|---|
| 36 | $CF_3$ | H | $CH_3$ | $CH_3$ | 137–8 |
| 37 | $CF_3$ | H | $CH_3$ | $C_2H_5$ | 132–4 |
| 38 | $H_3CS$ | H | $CH_3$ | $CH_3$ | 157–9 |

EXAMPLE 39

1-Methyl-3-[5-Allylthio-2-(1,3,4-Thiadiazolyl)] Urea

2-Amino-5-allylthio-1,3,4-thiadiazole (5 g, 0.03 mole, m.pt. 116°–118° C.), prepared by allylating 2-amino-5-mecapto-1,3,4-thiadiazole with allyl bromide, was slurried with acetone (50 ml) in a 125 ml pressure bottle. Methyl isocyanate (1.8 g, 0.032 mole) was added thereto and the resulting mixture was heated by placing the bottle in a steam bath for 2½ hours. The bottle was removed from the bath and the contents were cooled to about 20° C.; as the contents cooled, a white solid separated from the reaction mixture.

The solid was separated by filtering the reaction mixture, and was dried in a vacuum oven at 60° C. The solid weighed 4.1 grams (61% yield) and had a melting point of 171°–172° C. Additional solid can be obtained by concentrating the filtrate, by heating the filtrate to remove acetone therefrom.

The solid is 1-methyl-3-[5-allylthio-2-(1,3,4-thiadizolyl] urea as indicated by IR and NMR spectra,

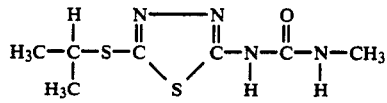

The 2-amino-5-mercapto-1,3,4-thiadiazole (m.pt. 234° C.) was prepared by reaction of carbon disulfide with thiosemicarbazide in dimethylformamide.

EXAMPLE 40

1-Methyl-3-[5-Isopropylthio-2-(1,3,4-Thiadiazolyl)] Urea

2-Amino-5-isopropylthio-1,3,4-thiadiazole (5 g, 0.03 mole, m.pt. 145°–147° C.), prepared by alkylating 2-amino-5-mercapto-1,3,4-thiadiazole with 2-bromopropane, was slurried with acetone (50 ml) in a 125 ml pressure bottle. Methyl isocyanate (1.8 g, 0.032 mole) was added thereto and the resulting solution was heated by placing the bottle in a steam bath for 3 hours. The bottle was removed from the bath and the contents were cooled by placing the bottle in an ice bath. As the bottle was cooled, a white solid separated from the reaction mixture. The solid was isolated by filtering the reaction mixture. The solid was dried in a vacuum oven at 60° C. The solid weighed 3.9 g (58% yield) and had a melting point of 170°–172° C. Again, additional solid can be obtained by concentrating the filtrate, i.e., the acetone solution containing a part of the reaction mixture. The IR and the NMR spectra support the proposed structure:

H   N——N        O
|   ‖   ‖        ‖
H₃C—C—S—C   C—N—C—N—CH₃
|       \\ /   |       |
H₃C      S    H       H

EXAMPLE 41

1-Methyl-3-[5-n-Propylthio-2-(1,3,4-Thiadiazolyl)]Urea

2-Amino-5-n-propylthio-1,3,4-thiadiazole (5.0 g, 0.03 mole, m.pt. 112°–114° C.), prepared by allkylating 2-amino-5-mercapto-1,3,4-thiadiazole with 1-bromopropane, was slurried with acetone (50 ml) in a 125 ml pressure bottle. Methyl isocyanate (1.8 g, 0.032 mole) was added thereto and the resulting mixture was heated by placing the bottle in a steam bath for 2½ hours. The bottle was removed from the bath and was cooled in an ice bath, whereupon a white solid separated. The white solid was filtered and dried in a vacuum oven at 60° C. The solid weighed 5.4 g (yield 78%), and had a melting point of 173°–75° C. The IR and NMR spectra support the proposed structure:

$$H_3C-CH_2-CH_2-S-\underset{S}{\overset{\overset{N=\!=\!=N}{\|}}{C}}\diagdown\underset{}{\overset{}{}}\diagup\underset{H}{\overset{}{C}}-\underset{H}{\overset{}{N}}-\overset{\overset{O}{\|}}{C}-N-CH_3$$

HERBICIDE TESTS

Pre- and Post-Emergence Herbicide Tests

Method of Propagating Test Species

Crabgrass (CG)—*Digitaria sanguinalis*
Yellow foxtail grass (YF)—*Setaria glauca*
Johnson grass (JG)—*Sorgum helepense*
Barnyard grass (BG)—*Echinochloa crus-calli*
Amaranth pigweed (PW)—*Amaranthus retroflexus*
Turnip (TP)—*Brassica sp.*
Cotton (CT)—*Gossypium hirsutum* var. DPL smooth leaf
Corn (CN)—*Zea Mays*
Bean (BN)—*Phaseolus vulgaris* var. Black Valentine All crop and weed species were planted individually in 3" plastic pots containing potting soil. Four seeds each of corn, cotton, and snapbeans were seeded to a depth equal to the diameter of the seed. All other species were surface seeded and sprinkled with screened soil in an amount sufficient to cover the seed. Immediately after planting, all pots were watered by sub-irrigation in greenhouse trays. Pots for the pre-emergence phase were seeded one day before treatment.

Planting dates for the post-emergence phase were varied so that all seedlings would reach the desired stage of development simultaneously. The proper stage of seedling development for treatment in the post-emergence phase is as follows:

Grasses: 2" in height
Pigweed and turnips: 1 or 8 true leaves above visible cotyledons.
Cotton: first true leaf 1" in length; expanded cotyledons.
Corn: 3"-4" in height.
Beans: primary leaves expanded, growing point at primary leaf nodes.

METHOD OF TREATMENT

Compounds were tested at rates of application equivalent to 8 lbs. of actual compound per acre in a spray volume of 38 gallons per acre. Spray hood constants required to deliver the above volume are as follows:
Belt speed: 2 mph
Air pressure: adjusted to provide 38 gal/per acre delivery.
Nozzle tip: to provide uniform cross-section flat spray.
Formulations for spray application were prepared in 50 ml volumes with the following three components:
1. 1.24 grams of compound (8 lbs/acre rate).
2. 49 ml acetone or acetone-water combination.
3. 1 ml of Tween-20.

Formulations for the 4 lbs/acre rate were prepared by adjusting the amount of active ingredient accordingly.

Spray applications were made in a hood containing a removable belt and fixed spray nozzle. For passage through the spray hood, one pot of each specie (pre-emergence phase) was placed on the rear half of the flat. Treatments were removed to the greenhose after spraying. Watering during the observation period was done only by sub-irrigation.

METHOD OF RECORDING RESULTS

Two weeks after treatment, pre- and post-emergence injury or control was visually rated, and the results were as shown in the following tables. Pre-emergence data are provided in TABLE III and post-emergence data are provided in TABLE IV, for compounds having the formula illustrated in TABLE I. Correspondingly, pre-emergence and post-emergence data, respectively, are set forth in TABLES V AND VI, for compounds having the formula illustrated in TABLE II.

TABLE III

| | PRE-EMERGENCE ACTIVITY, % CONTROL | | | | | | | | |
|---|---|---|---|---|---|---|---|---|---|
| EXAMPLE | RATE LB/ACRE | CG | YF | JG | BG | PW | TP | CT | CN | BN |
| 1 | 8 | 100 | 90 | 70 | 90 | 90 | 100 | 100 | 90 | 90 |
|   | 4 | 90 | 80 | 80 | 90 | 90 | 90 | 80 | 30 | 90 |
| 2 | 8 | 90 | 90 | 90 | 90 | 90 | 100 | 70 | 50 | 80 |
| 3 | 8 | 10 | — | 20 | 10 | 70 | 70 | 50 | 100 | 90 |
| 9 | 8 | 10 | 20 | 10 | 20 | — | 10 | 30 | 50 | 100 |
| 10 | 8 | 20 | 20 | 20 | 10 | — | 10 | 80 | 50 | 80 |
| 11 | 8 | 20 | 10 | 30 | 10 | — | 10 | 80 | 80 | 30 |
| 12 | 8 | 20 | 10 | 10 | 10 | 10 | 10 | 30 | 10 | 10 |
| 14 | 8 | 10 | 10 | 20 | 10 | 90 | 10 | 50 | 50 | 100 |
| 15 | 8 | 10 | 10 | 10 | 10 | — | 10 | 80 | 10 | 30 |
| 16 | 8 | 10 | 10 | 10 | 10 | — | 30 | 30 | 30 | 80 |
| 18 | 8 | 10 | — | 10 | 20 | 10 | 50 | 30 | 30 | 50 |
| 19 | 8 | 10 | — | 20 | 10 | 10 | 20 | 30 | 80 | 80 |
| 20 | 8 | 90 | — | 70 | — | 90 | 100 | 30 | 30 | 10 |
| 21 | 8 | 20 | — | 10 | 10 | 60 | 20 | 10 | 10 | 100 |
| 24 | 8 | 10 | 10 | 10 | 10 | 60 | 10 | 10 | 30 | 60 |
| 25 | 8 | 20 | 10 | 10 | 10 | 10 | 10 | 100 | 10 | 70 |
| 26 | 8 | 100 | — | — | 50 | — | 30 | 100 | 50 | 30 |
| 28 | 8 | 40 | 30 | 20 | 50 | 30 | 0 | 40 | 10 | 80 |
| 29 | 8 | 20 | 10 | 10 | 10 | 10 | 0 | 30 | 30 | 80 |
| 30 | 8 | 20 | 10 | 10 | 10 | 10 | — | 10 | 10 | 50 |
| 31 | 8 | 70 | 70 | 20 | 30 | 20 | 30 | 30 | 10 | 80 |
| 32 | 8 | 90 | 90 | 70 | 90 | 100 | 90 | 50 | 70 | 80 |
| 33 | 8 | 90 | 80 | 70 | 80 | 70 | 100 | 50 | 70 | 90 |
|   | 4 | 90 | 90 | 60 | 90 | 60 | 100 | 50 | 20 | 90 |
|   | 2 | 90 | 70 | 80 | 70 | 50 | 90 | 40 | 20 | 100 |
| 34 | 8 | 10 | 20 | 20 | 10 | — | 20 | 40 | 10 | 80 |
| 35 | 8 | 10 | 10 | 10 | 10 | 10 | 10 | 100 | 10 | 60 |
| 39 | 2 | 60 | — | 30 | 50 | — | 70 | 50 | 10 | 40 |

TABLE III-continued

| | | PRE-EMERGENCE ACTIVITY, % CONTROL | | | | | | | | |
|---|---|---|---|---|---|---|---|---|---|---|
| EXAMPLE | RATE LB/ACRE | CG | YF | JG | BG | PW | TP | CT | CN | BN |
| 40 | 4 | 50 | — | 30 | 40 | — | 100 | 30 | — | 10 |
| 41 | 2 | 90 | — | 70 | 50 | — | 60 | 50 | 10 | 30 |

TABLE IV

| | | POST-EMERGENCE ACTIVITY, % CONTROL | | | | | | | | |
|---|---|---|---|---|---|---|---|---|---|---|
| EXAMPLE | RATE LB/ACRE | CG | YF | JG | BG | PW | TP | CT | CN | BN |
| 1 | 8 | 100 | 100 | 100 | 100 | 100 | 100 | 100 | 100 | 100 |
| | 4 | 90 | 90 | 90 | 100 | 100 | 100 | 100 | 100 | 100 |
| | 2 | 60 | 50 | 90 | 70 | 100 | 80 | 100 | 70 | 100 |
| 2 | 8 | 60 | 60 | 40 | 60 | 90 | 80 | 90 | 100 | 60 |
| | 4 | 80 | 90 | 30 | 90 | 100 | 90 | 90 | 100 | 70 |
| | 2 | 100 | 90 | 90 | 90 | 100 | 100 | 100 | 100 | 8 |
| 3 | 8 | 20 | 20 | 20 | 20 | 100 | 100 | 90 | 20 | 6 |
| 9 | 8 | 60 | 30 | 80 | 40 | 100 | 60 | 50 | 30 | 7 |
| 10 | 8 | 50 | 20 | 30 | 40 | 100 | 60 | 60 | 40 | 5 |
| 11 | 8 | 50 | 20 | 30 | 40 | 100 | 60 | 60 | 40 | 5 |
| 12 | 8 | 50 | 40 | 40 | 50 | 70 | 70 | 90 | 40 | 10 |
| 14 | 8 | 10 | 10 | 20 | 10 | 90 | 10 | 50 | 50 | 10 |
| 15 | 8 | 30 | 20 | 20 | 20 | 100 | 50 | 60 | 20 | 4 |
| 16 | 8 | 20 | 20 | 20 | 20 | 100 | 40 | 20 | 20 | 40 |
| 18 | 8 | 20 | 20 | 20 | 20 | 40 | 40 | 50 | 20 | 50 |
| 19 | 8 | 20 | 20 | 20 | 10 | 40 | 50 | 40 | 20 | 50 |
| 20 | 8 | 20 | — | 20 | 20 | 100 | 90 | 80 | 30 | 50 |
| 21 | 8 | 30 | — | 30 | 20 | 20 | 20 | 50 | 20 | 60 |
| 24 | 8 | 30 | 20 | 20 | 20 | 90 | 60 | 70 | 20 | — |
| 25 | 8 | 30 | 20 | 30 | 20 | 40 | 30 | 100 | 30 | 100 |
| 26 | 8 | 100 | 90 | 100 | 60 | 100 | 100 | 90 | 40 | 100 |
| | 4 | 100 | 100 | 80 | 100 | 100 | 100 | 90 | 100 | 100 |
| | 2 | 50 | 60 | 30 | 10 | 90 | 60 | 100 | 20 | 100 |
| 28 | 8 | 20 | 20 | 20 | 20 | 30 | 50 | 70 | 20 | 50 |
| 29 | 8 | 30 | 20 | 20 | 20 | 40 | 40 | 60 | 20 | 100 |
| 30 | 8 | 20 | 20 | 20 | 20 | 50 | 40 | 70 | 20 | 100 |
| 31 | 8 | 30 | 30 | 30 | 20 | 90 | 50 | 100 | 20 | 100 |
| 32 | 8 | 100 | 90 | 90 | 100 | 100 | 90 | 100 | 60 | 100 |
| 33 | 8 | 90 | 90 | 40 | 100 | 100 | 100 | 100 | 100 | 100 |
| | 4 | 60 | 100 | 50 | 70 | 100 | 80 | 100 | 10 | 100 |
| | 2 | 90 | 70 | 80 | 70 | 50 | 90 | 40 | 20 | 100 |
| 34 | 8 | 10 | 30 | 30 | 10 | 20 | 40 | 50 | 50 | 60 |
| 35 | 8 | 10 | 10 | 10 | 10 | 100 | 20 | 50 | 10 | 30 |
| 39 | 2 | 80 | — | 80 | 90 | — | 80 | 100 | 50 | 100 |
| 40 | 4 | 90 | — | 70 | 50 | — | 100 | 100 | 40 | 100 |
| 41 | 2 | 100 | — | 90 | 90 | — | 70 | 100 | 100 | 70 |

TABLE V

| | | PRE-EMERGENCE ACTIVITY, % CONTROL | | | | | | | | |
|---|---|---|---|---|---|---|---|---|---|---|
| EXAMPLE | RATE LB/ACRE | CG | YF | JG | BG | PW | TP | CT | CN | BN |
| 4 | 4 | 100 | 80 | 40 | 90 | 100 | 100 | 70 | 70 | 90 |
| 5 | 8 | 100 | 90 | 50 | 80 | 100 | 100 | 90 | 70 | 90 |
| 36 | 8 | 90 | 90 | 90 | 90 | 90 | 100 | 90 | 30 | 100 |
| | 4 | 90 | 90 | 40 | 100 | 100 | 100 | 90 | 40 | 80 |
| | 2 | 100 | 100 | 70 | 80 | 90 | 100 | 80 | 30 | 90 |
| 37 | 8 | 90 | 90 | 60 | 90 | 100 | 100 | 60 | 50 | 90 |
| | 4 | 90 | 80 | 70 | 60 | 100 | 100 | 40 | 40 | 70 |
| | 2 | 90 | 70 | 60 | 50 | 90 | 100 | 40 | 30 | 80 |
| 38 | 8 | 100 | 100 | 80 | 100 | 90 | 100 | 90 | 80 | 100 |

TABLE VI

| | | POST-EMERGENCE ACTIVITY, % CONTROL | | | | | | | | |
|---|---|---|---|---|---|---|---|---|---|---|
| EXAMPLE | RATE LB/ACRE | CG | YF | JG | BG | PW | TP | CT | CN | BN |
| 4 | 4 | 80 | 90 | 40 | 60 | 100 | 100 | 100 | 100 | 100 |
| 5 | 8 | 100 | 100 | 90 | 100 | 100 | 100 | 100 | 100 | 100 |
| 36 | 8 | 100 | 100 | 100 | 100 | 100 | 100 | 100 | 100 | 100 |
| | 4 | 90 | 100 | 80 | 100 | 100 | 100 | 100 | 100 | 100 |
| | 2 | 70 | 100 | 80 | 100 | 100 | 100 | 100 | 70 | 100 |
| 37 | 8 | 90 | 90 | 70 | 90 | 100 | 100 | 100 | 80 | 100 |
| | 4 | 40 | 50 | 30 | 30 | 100 | 90 | 100 | 30 | 100 |
| | 2 | 30 | 30 | 20 | 20 | 90 | 90 | 100 | 20 | 90 |

TABLE VI-continued

| EXAMPLE | RATE LB/ACRE | POST-EMERGENCE ACTIVITY, % CONTROL ||||||||
| | | CG | YF | JG | BG | PW | TP | CT | CN | BN |
|---|---|---|---|---|---|---|---|---|---|---|
| 38 | 8 | 80 | 100 | 80 | 90 | 100 | 100 | 100 | 100 | 100 |

Data for each compound given in TABLES III-VI reveals that several of the compounds are extremely effective when applied to a variety of crops and weed species. Typical of such compounds are: 1, 2, 5, 26, 36, and 37. Other compounds appear to be more selective when applied to a certain crop or weed species rather than have wide application; such compounds are illustrated by: 9, 15, 16, 20, 21, 25, and 35. Still others are more selective in that they control post-emergence growth, while have little effect in regard to pre-emergence; this is illustrated by compound 12. The converse of this relationship is shown by compound 19.

Additional examples of compounds suitable for use as herbicides are given in TABLE VII. The compounds are prepared by the method described in EXAMPLE 1, except for the compound of EXAMPLE 70. In each compound X is oxygen.

TABLE VII

| Example | R | $R_1$ | $R_2$ | $R_3$ | M. Pt., °C. |
|---|---|---|---|---|---|
| 42 | $(CH_3)_3C$ | H | $CH_3$ | $CH_3$ | 155-161 |
| 43 | $(CH_3)_3C$ | $CH_3$ | $CH_3$ | $CH_3$ | oil |
| 44 | $(CH_3)_2CHCH_2S$ | H | $CH_3$ | H | 142-4 |
| 45 | $C_4H_9S$ | H | $CH_3$ | H | 154-6 |
| 46 | $\phi CH_2S$ | H | $CH_3$ | H | 195-7 |
| 48 | $CH_3CH_2\overset{CH_3}{\underset{|}{C}}HS$ | H | $CH_3$ | H | 128-130 |
| 49 | $CH_2=\overset{CH_3}{\underset{|}{C}}CH_2S$ | H | $CH_3$ | H | 149-151 |
| 50 | $CH_3CH_2\overset{CH_3}{\underset{|}{C}}=CHCH_2S$ | H | $CH_3$ | H | 131-3 |
| 51 | $(CH_3)_2CHCH_2CH_2S$ | H | $CH_3$ | H | 126-8 |
| 52 | $NCCH_2CH_2S$ | H | $CH_3$ | H | 168-170 |
| 53 | $\phi CH_2CH_2S$ | H | $CH_3$ | H | 168-9 |
| 54 | $CH_3\overset{O}{\underset{\|}{C}}CH_2S$ | H | $CH_3$ | H | 166-8 |
| 55 | $O_2N-\langle\!\langle\ \rangle\!\rangle-CH_2S$ | H | $CH_3$ | H | 244-5 |
| 56 | $CH_3O\overset{O}{\underset{\|}{C}}CH_2S$ | H | $CH_3$ | H | 153-5 |
| 57 | $CClF_2$ | H | $CH_3$ | H | 142-5 |
| 58 | $C_6H_{13}SO_2$ | H | $CH_3$ | H | 150-2 |
| 59 | $C_5H_{11}S$ | H | $CH_3$ | H | 131-3 |
| 60 | $C_6H_{13}S$ | H | $CH_3$ | H | 131 |
| 61 | $ClCH_2CH_2CH_2S$ | H | $CH_3$ | H | 209-211 |
| 62 | $C_3H_7SO_2$ | H | $CH_3$ | H | 217-9 |
| 63 | $C_5H_{11}SO_2$ | H | $CH_3$ | H | 168-70 |
| 64 | $C_4H_9SO_2$ | H | $CH_3$ | H | 195-6 |
| 65 | $C_3H_7S$ | $CH_3$ | $CH_3$ | $CH_3$ | 44-47 |
| 66 | $CHF_2$ | H | $CH_3$ | H | 208-9 |
| 67 | $CF_3CF_2$ | H | $CH_3$ | H | 161-2 |
| 68 | $C_3H_7S$ | H | $CH_3$ | $CH_3$ | 106-8 |
| 69 | $CF_3$ | H | H | H | 229-231 |
| 70 | | | | | |

The compound of EXAMPLE 70 is prepared by dissolving potassium cyanate in water and adding the resulting solution to a solution of 2-amino-5-methyl-1,3,4-thiadiazole in acetic acid. (A. Ermili and I. Cortese, Farmaco, Ed. Sci., 22 (6), 393-401 (1967).) The acetic acid solution was kept cool during the addition of the cyanate solution. The melting point of the desired product is 229°-231° C.

Results of herbicide tests made with compounds within the group shown in TABLE VII are set forth in TABLES VII and IX. The tests were made following the same procedure as described above in connection with TABLES III-VI.

TABLE VIII

| EXAMPLE | RATE LB/ACRE | PRE-EMERGENCE ACTIVITY, % CONTROL ||||||||
| | | CG | YF | JG | BG | PW | TP | CT | CN | BN |
|---|---|---|---|---|---|---|---|---|---|---|
| 42 | 8 | 90 | 90 | 100 | 90 | 100 | 100 | 90 | 90 | 100 |
| | 4 | 90 | 80 | 90 | 90 | 100 | 90 | 70 | 60 | 90 |
| | 2 | 90 | 90 | 70 | 80 | 100 | 100 | 30 | 0 | 40 |
| 43 | 4 | 100 | 100 | 90 | 100 | 100 | 100 | 90 | 90 | 90 |
| 62 | 4 | 90 | — | 40 | 60 | — | 40 | 100 | 0 | 50 |
| | 2 | 90 | — | 40 | 60 | — | 80 | 100 | 0 | 60 |
| 63 | 4 | 90 | — | 50 | 30 | — | 30 | 50 | 0 | 0 |
| | 2 | 90 | — | 40 | 50 | — | 70 | 0 | 0 | 50 |
| 66 | 4 | 100 | — | 100 | 100 | 100 | 100 | 100 | 50 | 100 |
| | 2 | 30 | — | 20 | 30 | 100 | 50 | 80 | 0 | 100 |
| 67 | 4 | 90 | — | 50 | — | 100 | 100 | 80 | 70 | 90 |
| | 2 | 80 | — | 40 | 50 | — | 60 | 0 | 0 | 0 |
| 68 | 4 | 90 | — | 30 | — | 100 | 60 | 90 | 50 | 100 |
| | 2 | 50 | — | 20 | 30 | 100 | 60 | 60 | 30 | 0 |
| 69 | 8 | 100 | — | 70 | — | 100 | 100 | 90 | 50 | 100 |
| | 4 | 90 | — | 40 | 60 | 100 | 50 | 30 | 0 | 0 |
| | 2 | 90 | — | 20 | 40 | — | 90 | 50 | 30 | 0 |
| 70 | 10 | 10 | — | — | — | — | 10 | — | — | — |
| | 5 | 10 | — | — | — | — | 10 | — | — | — |

TABLE IX

POST-EMERGENCE ACTIVITY, % CONTROL

| EXAMPLE | RATE LB/ACRE | CG | YF | JG | BG | PW | TP | CT | CN | BN |
|---|---|---|---|---|---|---|---|---|---|---|
| 42 | 8 | 100 | 100 | 100 | 100 | 100 | 100 | 100 | 100 | 100 |
|  | 4 | 70 | 90 | 90 | 90 | 100 | 100 | 100 | 70 | 100 |
|  | 2 | 40 | 90 | 70 | 90 | 100 | 100 | 100 | 70 | 80 |
| 43 | 4 | 100 | 100 | 100 | 100 | 100 | 100 | 100 | 100 | 100 |
| 44 | 2 | 90 | — | 80 | 90 | — | 80 | 100 | 60 | 100 |
|  | 1 | 80 | — | 60 | 80 | — | 40 | 100 | 60 | 80 |
| 45 | 2 | 90 | — | 90 | 80 | — | 70 | 100 | 60 | 100 |
|  | 1 | 90 | — | 60 | 90 | — | 50 | 100 | 70 | 90 |
| 46 | 4 | 70 | — | 70 | 70 | — | 100 | 100 | 30 | 90 |
| 48 | 4 | 70 | 30 | 60 | 40 | — | 70 | 100 | 30 | 50 |
| 49 | 4 | 80 | 40 | 40 | 40 | — | 90 | 100 | 40 | 50 |
|  | 2 | — | — | — | — | 100 | 70 | — | — | — |
| 50 | 4 | 50 | — | 30 | 20 | 90 | 80 | 80 | 30 | 100 |
|  | 2 | — | — | — | — | 90 | 60 | — | — | — |
| 51 | 4 | 60 | — | 40 | 70 | 90 | 90 | 100 | 50 | 100 |
|  | 2 | — | — | — | — | 90 | 80 | — | — | — |
| 52 | 4 | 70 | — | 20 | 20 | 80 | 80 | 100 | 100 | 100 |
| 53 | 4 | 60 | — | 30 | 20 | 90 | 90 | 100 | 100 | 100 |
|  | 2 | — | — | — | — | 90 | 70 | — | — | — |
| 54 | 4 | 50 | — | 30 | 30 | 90 | 80 | 90 | 30 | 100 |
|  | 2 | — | — | — | — | 60 | 60 | — | — | — |
| 55 | 4 | 40 | — | 30 | 20 | 90 | 90 | 50 | 20 | 100 |
|  | 2 | — | — | — | — | 90 | 60 | — | — | — |
| 56 | 4 | 30 | — | 20 | 20 | 60 | 70 | 60 | 30 | 50 |
| 57 | 8 | 60 | — | 40 | 40 | 90 | 100 | 90 | 40 | 100 |
| 58 | 4 | 50 | — | 30 | 20 | — | 80 | 50 | 20 | 70 |
| 59 | 4 | 90 | — | 80 | 70 | — | 100 | 100 | 40 | 100 |
| 60 | 4 | 80 | — | 70 | 40 | — | 100 | 70 | 60 | 100 |
|  | 2 | — | — | — | — | — | 100 | — | — | — |
| 61 | 4 | 90 | — | 60 | 70 | 90 | 80 | 100 | 30 | 100 |
|  | 2 | 20 | — | 20 | 40 | 90 | 100 | 100 | 40 | 100 |
| 62 | 4 | 100 | — | 100 | 80 | — | 100 | 100 | 50 | 100 |
|  | 2 | 100 | — | — | — | — | 100 | 90 | 100 | 100 |
| 63 | 4 | 90 | — | 70 | 70 | — | 100 | 100 | 50 | 100 |
|  | 2 | 80 | — | — | — | — | 100 | 90 | 60 | 100 |
| 64 | 4 | 90 | — | 50 | 60 | — | 90 | 70 | 30 | 90 |
| 65 | 4 | 90 | — | 60 | 90 | — | 100 | 70 | 30 | 100 |
| 66 | 4 | 100 | — | 60 | 70 | 100 | 100 | 100 | 100 | 100 |
|  | 2 | 50 | — | 50 | 60 | 100 | 100 | 100 | 30 | 90 |
| 67 | 4 | 80 | — | 90 | — | 100 | 100 | 100 | 70 | 100 |
|  | 2 | 80 | — | 40 | 80 | — | 100 | 100 | 40 | 90 |
| 68 | 4 | 100 | — | 80 | — | 100 | 100 | 100 | 100 | 100 |
|  | 2 | 90 | — | 80 | 60 | 100 | 100 | 80 | 50 | 90 |
| 69 | 8 | 100 | — | 100 | — | 100 | 100 | 100 | 100 | 100 |
|  | 4 | 90 | — | 80 | 80 | 100 | 100 | 100 | 50 | 100 |
|  | 2 | 100 | — | 70 | 90 | — | 100 | 100 | 80 | 100 |
| 70 | 10 | 20 | — | — | — | — | 80 | 20 | — | 50 |
|  | 5 | 20 | — | — | — | — | 80 | 20 | — | 50 |

Additional illustrative examples of compounds for use as herbicides are given in TABLE X. The compounds are prepared by the method described in EXAMPLE 1. In each compound X is oxygen.

TABLE X

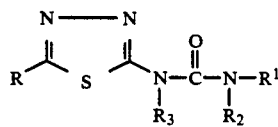

| EXAMPLE | R | R¹ | R² | R³ | M. Pt., °C. |
|---|---|---|---|---|---|
| 71 | 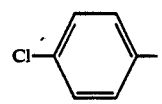 | H | CH₃ | H | >280° |
| 72 | 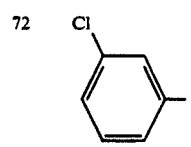 | H | CH₃ | H | >280° |

TABLE X-continued

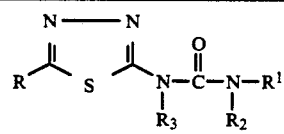

| EXAMPLE | R | R¹ | R² | R³ | M. Pt., °C. |
|---|---|---|---|---|---|
| 73 |  CF₃ | H | CH₃ | H | >280° |
| 74 | 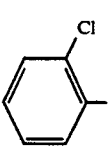 Cl | H | CH₃ | H | 205° |

TABLE X-continued $$\underset{R}{\overset{N\text{———}N}{\|}}\underset{S}{\overset{}{\diagdown}}\underset{R_3}{\overset{}{\diagup}}\underset{}{\overset{O}{\|}}\underset{R_2}{\overset{}{N-R^1}}$$

| EXAMPLE | R | $R^1$ | $R^2$ | $R^3$ | M. Pt., °C. |
|---|---|---|---|---|---|
| 75 | 2,4-dichlorophenyl | H | $CH_3$ | H | >280° |
| 76 | 4-methylphenyl | H | $CH_3$ | H | 265° |
| 77 | 2,3-dichlorophenyl | H | $CH_3$ | H | >280° |
| 78 | $C_8H_{17}S$ | H | $CH_3$ | H | 120–2° |
| 79 | $(C_2H_5OC)_2CHS$ (with C=O) | H | $CH_3$ | H | 280° |
| 80 | $C_2H_5SCH_2CH_2S$ | H | $CH_3$ | H | 178–9° |
| 81 | $C_2H_5SO_2$ | H | $CH_3$ | H | 209–11° |
| 82 | $(CH_3)_2CH$ | H | $CH_3$ | H | 147–9° |
| 83 | $CH_3CH_2CH_2CH(CH_3)$ | H | $CH_3$ | H | 128–30° |
| 84* | $CH_3$ | H | H | H | >250° |
| 85 | cyclopropyl | H | $CH_3$ | H | 191–4° |
| 86 | $(CH_3)_3C$ | H | $CH_3$ | H | 202–204° |
| 87 | 4-chlorobenzyl-S ($Cl\text{-}C_6H_4\text{-}CH_2S$) | H | $CH_3$ | H | 190–192° |
| 88 | $NCCH_2S$ | H | $CH_3$ | H | 209–10° |
| 89 | $C_2H_5S$ | H | $CH_3$ | $CH_3$ | 117–119° |
| 90 | $n\text{-}C_4H_9S$ | H | $CH_3$ | $CH_3$ | 85–87° |
| 91 | $C_2H_5SO_2$ | H | $CH_3$ | $CH_3$ | 155–157° |
| 92 | $n\text{-}C_4H_9SO_2$ | H | $CH_3$ | $CH_3$ | 127–129° |

*Comparative Example

In TABLES XI and XII, results of herbicide tests are recited. These were obtained with compounds identified in TABLE X and the tests were made by following the same procedure as described in connection with TABLES III–VI.

TABLE XI

PRE-EMERGENCE ACTIVITY, % CONTROL

| EXAMPLE | RATE LBS./ACRE | CG | YF | JG | BG | PW | TP | CT | CN | BN |
|---|---|---|---|---|---|---|---|---|---|---|
| 71 | 8 | 0 | 0 | 0 | 20 | — | 0 | 90 | 0 | 50 |
| 72 | 8 | 0 | — | 0 | 0 | — | 0 | 80 | 30 | 100 |
| 73 | 4 | 0 | — | 0 | 0 | — | 60 | 100 | 50 | 80 |
| 74 | 8 | 20 | — | 0 | 30 | — | 50 | 100 | 0 | 100 |
| 75 | 8 | 0 | — | 0 | 0 | — | 40 | 30 | 0 | 100 |
| 76 | 8 | 20 | — | 0 | 30 | — | 40 | 100 | 50 | 80 |
| 77 | 8 | 0 | — | 0 | 20 | — | 20 | 30 | 20 | 20 |
| 78 | 1 | 20 | — | 0 | 0 | — | 0 | 30 | 0 | 80 |
| 79 | 4 | 20 | — | 20 | — | 0 | 20 | 50 | 20 | 90 |
| 80 | 8 | 50 | — | 20 | 20 | — | 0 | 50 | 0 | 100 |
| 81 | 4 | 90 | — | 40 | 60 | — | 80 | 100 | 0 | 60 |
|  | 2 | 90 | — | 40 | 60 | — | 80 | 100 | 0 | 60 |
| 82 | 4 | 30 | — | 0 | — | — | 20 | — | — | — |
| 84 | 10 | 0 | — | 50 | — | — | 0 | — | — | — |
| 83 | 4 | 90 | — | 60 | 50 | 80 | 10 | 10 | 10 | — |
| 85 | 4 | 0 | — | — | 0 | — | 0 | — | — | — |
| 86 | 8 | 100 | — | 50 | 80 | — | 100 | 50 | 60 | 100 |
|  | 2 | 90 | 90 | 60 | 60 | 100 | 100 | 10 | 10 | 30 |
| 87 | 8 | 10 | — | 20 | 20 | 70 | 10 | 50 | 10 | 100 |
| 88 | 4 | 10 | — | 10 | 10 | 10 | 70 | 50 | 10 | 100 |
| 89 | 4 | 100 | — | 70 | 100 | 100 | 90 | 50 | 50 | 10 |
|  | 2 | 90 | — | 80 | 80 | 100 | 80 | 10 | 40 | 10 |
|  | 1 | 90 | — | 50 | 80 | 100 | 70 | 10 | 50 | 10 |
|  | 0.5 | 50 | — | 40 | 30 | 70 | 30 | 10 | 10 | 10 |
| 90 | 4 | 90 | — | 50 | 90 | 100 | 80 | 50 | 30 | 70 |
|  | 2 | 90 | — | 50 | 90 | 100 | 60 | 30 | 10 | 40 |
|  | 1 | 10 | — | 10 | 10 | 30 | 10 | 10 | 10 | 10 |
|  | 0.5 | 10 | — | 10 | 10 | 10 | 10 | 10 | 10 | 10 |
| 91 | 4 | 100 | — | 100 | 100 | 100 | 100 | 90 | 60 | 100 |
|  | 2 | 90 | — | 60 | 90 | 100 | 90 | 50 | 50 | 70 |
|  | 1 | 90 | — | 50 | 60 | 90 | 60 | 50 | 50 | 70 |
|  | 0.5 | 80 | — | 50 | 30 | 40 | 60 | 30 | 10 | 10 |
| 92 | 4 | 100 | — | 60 | 90 | 50 | 90 | 10 | 10 | 10 |
|  | 2 | 100 | — | 30 | 70 | 30 | 90 | 10 | 10 | 10 |
|  | 1 | 60 | — | 10 | 50 | 10 | 60 | 10 | 10 | 10 |

TABLE XI-continued

| | | PRE-EMERGENCE ACTIVITY, % CONTROL | | | | | | | | |
|---|---|---|---|---|---|---|---|---|---|---|
| EXAMPLE | RATE LBS./ACRE | CG | YF | JG | BG | PW | TP | CT | CN | BN |
| | 0.5 | 40 | — | 10 | 10 | 10 | 10 | 10 | 10 | 10 |

TABLE XII

| | | PRE-EMERGENCE ACTIVITY, % CONTROL | | | | | | | | |
|---|---|---|---|---|---|---|---|---|---|---|
| EXAMPLE | RATE LBS./ACRE | CG | YF | JG | BG | PW | TP | CT | CN | BN |
| 71 | 8 | 20 | 30 | 20 | 20 | 20 | 20 | 0 | 0 | 50 |
| 72 | 8 | 30 | 30 | 20 | 40 | — | 40 | 30 | 0 | 20 |
| 73 | 4 | 30 | — | 50 | 40 | — | 60 | 50 | 30 | 40 |
| 74 | 8 | 70 | — | 40 | 40 | — | 80 | 50 | 40 | 80 |
| 75 | 8 | 50 | — | 30 | 40 | — | 80 | 50 | 30 | 100 |
| 76 | 8 | 40 | — | 30 | 40 | — | 60 | 50 | 30 | 50 |
| 77 | 8 | 40 | — | 30 | 30 | — | 30 | 80 | 30 | 40 |
| 78 | 1 | 30 | — | 30 | 40 | — | 100 | 80 | 40 | 100 |
| 79 | 4 | 30 | — | 30 | — | 40 | 40 | 90 | 40 | 60 |
| 80 | 8 | 90 | — | 60 | 50 | — | 100 | 80 | 0 | 100 |
| 81 | 4 | 100 | — | 100 | 80 | — | 100 | 100 | 50 | 100 |
| | 2 | 100 | — | — | — | — | 100 | 90 | 100 | 100 |
| 82 | 4 | 50 | — | — | — | — | 80 | 80 | — | 60 |
| 83 | 4 | 10 | — | — | — | — | 90 | 10 | — | 40 |
| 84 | 10 | 20 | — | — | — | — | 80 | 20 | — | 50 |
| 85 | 4 | 30 | — | — | — | — | 60 | 80 | — | 50 |
| 86 | 8 | 80 | — | 100 | — | — | 100 | 100 | 100 | 100 |
| | 2 | 50 | 70 | 80 | 50 | 100 | 100 | 100 | 40 | 100 |
| 87 | 8 | 20 | — | 10 | 20 | 40 | 60 | 70 | 10 | 100 |
| 88 | 4 | 20 | — | 20 | — | 20 | 40 | 50 | 20 | 30 |
| 89 | 4 | 90 | — | — | — | — | 100 | 100 | — | 100 |
| | 2 | 90 | — | — | — | — | 100 | 100 | — | 100 |
| | 1 | 50 | — | — | — | — | 100 | 100 | — | 100 |
| | 0.5 | 40 | — | — | — | — | 100 | 90 | — | 90 |
| 90 | 4 | 90 | — | — | — | — | 100 | 100 | — | 100 |
| | 2 | 90 | — | — | — | — | 100 | 100 | — | 100 |
| | 1 | 60 | — | — | — | — | 100 | 100 | — | 100 |
| | 0.5 | 30 | — | — | — | — | 90 | 100 | — | 90 |
| 91 | 4 | 100 | — | — | — | — | 100 | 100 | — | 100 |
| | 2 | 70 | — | — | — | — | 100 | 100 | — | 100 |
| | 1 | 60 | — | — | — | — | 100 | 100 | — | 100 |
| | 0.5 | 40 | — | — | — | — | 100 | 100 | — | 100 |
| 92 | 4 | 90 | — | — | — | — | 100 | 100 | — | 100 |
| | 2 | 90 | — | — | — | — | 100 | 100 | — | 90 |
| | 1 | 30 | — | — | — | — | 100 | 100 | — | 80 |
| | 0.5 | 30 | — | — | — | — | 100 | 100 | — | 70 |

Toxicity studies reveal that the acute oral toxicity in rats for the compounds of Examples 1 and 86 are $LD_{50}$ of 436.2 and 2700 mg/kg.

Tests have also been made for the compound of Example 1 with Sinapis, oats and wheat. This test was conducted according to the following procedure.

Forty rows, 70 feet long, were planted to weeds and crops. Two rows were planted on each bed. Beds were 40 inches apart from center to center. The two rows were about 10 inches apart on each. Beds were rolled prior to planting to provide a uniform smooth surface. Soil temperature at a depth of 1½ inches was 66° F. at time of planting. Post-emergence applications were made by spraying bands across rows 10 feet wide using a self-propelled plot sprayer with a 10 foot boom equipped with Teejet 8001 flat spray nozzle tips and operated at 40 psi. A total of 84 fluid ounces of spray material was applied to three replicates. Each replicate plot was 10 feet wide by 66.67 feet long.

An additional 100 feet of crops and weeds shown in TABLES XIII and XIV were planted in the same manner as the above post-emergence plots. Soil temperature at planting was 65° C. at a depth of 1½ inches. A pre-emergence application was made the following day to these plots in the same manner as the post-emergence application above using the same application equipment and the same rate of total spray material.

Eight days after the application, readings were made on the effect of the chemicals on each crop and weed in the post-emergence treatment. A reading of 0 was recorded if no effect was observed; 10 recorded if the plants were completely killed, and readings of 1 to 9 for intermediate kills. A second reading of the post-emergence treatments was made 14 days after the application.

Readings were made 14 and 20 days after the pre-emergence application.

Results of the tests are provided in TABLES XIII and XIV below.

TABLE XIII

| | PRE-EMERGENCY ACTIVITY, % CONTROL | | |
|---|---|---|---|
| RATE LBS./ACRE | Sinapis | Oats | Wheat |
| 2 | 10 | 10 | 10 |
| 1 | 10 | 10 | 10 |

TABLE XIV

| POST-EMERGENCE ACTIVITY, % CONTROL | | | |
|---|---|---|---|
| RATE LBS./ACRE | Sinapis | Oats | Wheat |
| 2 | 10 | 9 | 10 |

I claim:
1. A compound of the formula

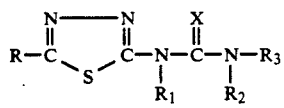

wherein
R is alkylsulfonyl ($C_1$-$C_6$),
$R_1$ is hydrogen,
$R_2$ is from the group consisting of hydrogen, alkyl ($C_1$-$C_4$), haloalkyl ($C_1$-$C_4$), alkoxy ($C_1$-$C_4$), alkenyl ($C_2$-$C_4$), alkynyl ($C_2$-$C_4$), aryl, and haloaryl,
$R_3$ is selected from the group consisting of hydrogen, alkyl ($C_1$-$C_4$), and cycloalkyl ($C_3$-$C_6$), and
X is selected from the group consisting of oxygen and sulfur.

2. A compound of the formula

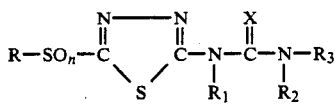

wherein
R is alkyl ($C_1$-$C_6$),
$R_1$ is hydrogen,
$R_2$ is hydrogen or alkyl ($C_1$-$C_4$),
$R_3$ is hydrogen or alkyl ($C_1$-$C_4$),
n is 2, and
X is oxygen or sulfur.

3. A compound of the formula

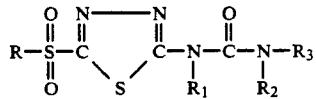

wherein R is an alkyl group having from 1 to 6 carbon atoms, $R_1$ is hydrogen $R_2$ is an alkyl group having from 1 to 4 carbon atoms, and $R_3$ is hydrogen or an alkyl group having from 1 to 4 carbon atoms.

4. A compound of claim 3 of the formula

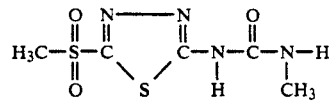

5. A compound of claim 3 of the formula

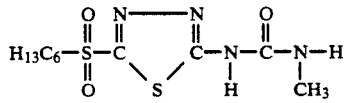

6. A compound of claim 3 of the formula

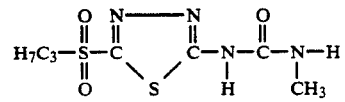

7. A compound of claim 3 of the formula

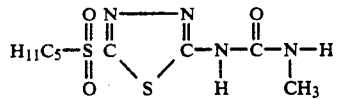

8. A compound of claim 3 of the formula

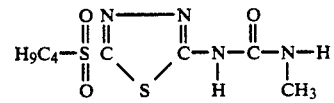

9. A compound of claim 3 of the formula

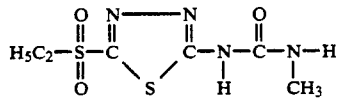

* * * * *